United States Patent [19]

Sitte

[11] Patent Number: 4,723,420
[45] Date of Patent: Feb. 9, 1988

[54] APPARATUS FOR TREATING SPECIMENS AT LOW TEMPERATURE

[75] Inventor: Hellmuth Sitte, Seefeld, Austria

[73] Assignee: C. Reichert Optische Werke A.G., Vienna, Austria

[21] Appl. No.: 752,988

[22] Filed: Jul. 8, 1985

[30] Foreign Application Priority Data

Jul. 12, 1984 [DE] Fed. Rep. of Germany ....... 3425744

[51] Int. Cl.⁴ .............................................. F25B 19/00
[52] U.S. Cl. ..................................... 62/514 R; 62/65; 62/373
[58] Field of Search ...................... 62/64, 65, 373, 376, 62/514 R

[56] References Cited

U.S. PATENT DOCUMENTS

| | | | |
|---|---|---|---|
| 2,214,009 | 9/1940 | Boester, Jr. | 62/376 |
| 3,027,734 | 4/1962 | Mills | 62/64 X |
| 4,232,453 | 11/1980 | Edelmann | 62/268 X |
| 4,471,629 | 9/1984 | Toledo-Pereyra | 62/64 |
| 4,487,033 | 12/1985 | Sakao et al. | 62/373 |
| 4,489,569 | 12/1984 | Sitte | 62/514 R |
| 4,530,816 | 7/1985 | Douglas-Hamilton | 62/64 X |
| 4,551,992 | 11/1985 | Sitte et al. | 62/514 R |

Primary Examiner—William E. Tapolcai
Attorney, Agent, or Firm—Alan H. Spencer

[57] ABSTRACT

Apparatus for treating biological specimens at low temperatures for subsequent microscopic examination comprises a container having a specimen treatment chamber disposed in a vessel adapted to contain liquid coolant. The specimen treatment chamber is adapted to receive a specimen to be treated and a specimen treatment medium. Precooling means is provided for precooling the specimen treatment medium before it is introduced to the specimen treatment chamber. The precooling means comprises a reservoir communicating with the specimen treatment chamber, and delivery means for delivering the specimen treatment medium to the reservoir. The reservoir and delivery means are arranged so that specimen treatment medium flowing through the reservoir and delivery means is cooled by the liquid coolant, and so that the specimen treatment medium can flow through the delivery means in countercurrent heat exchange with specimen treatment medium flowing from the reservoir to the specimen treatment chamber.

8 Claims, 13 Drawing Figures

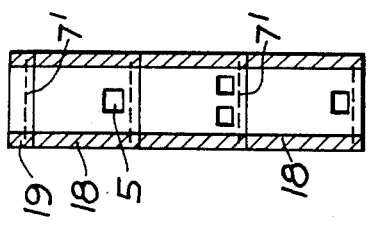
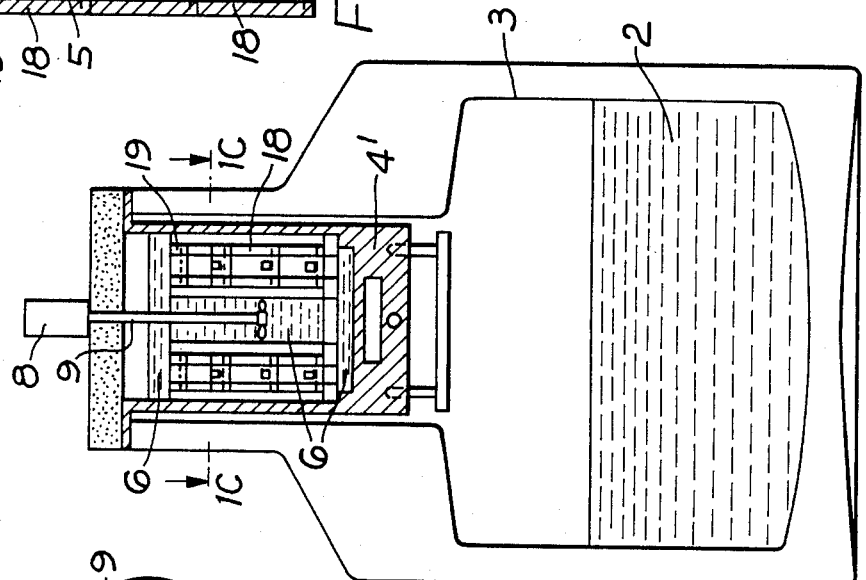
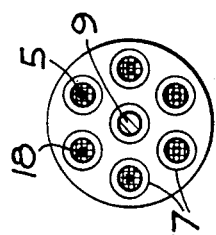
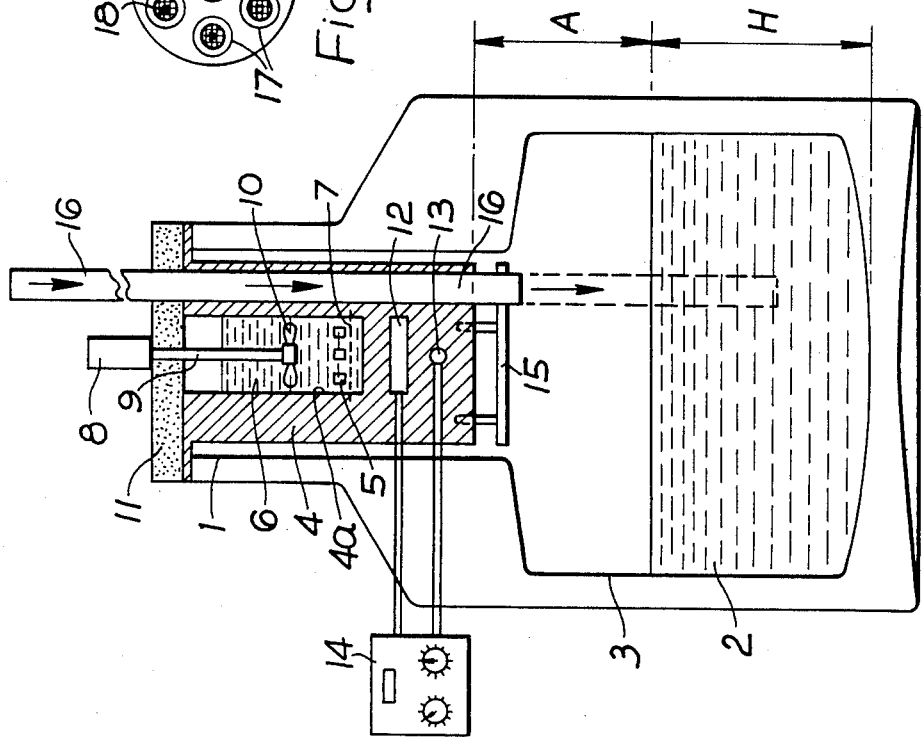

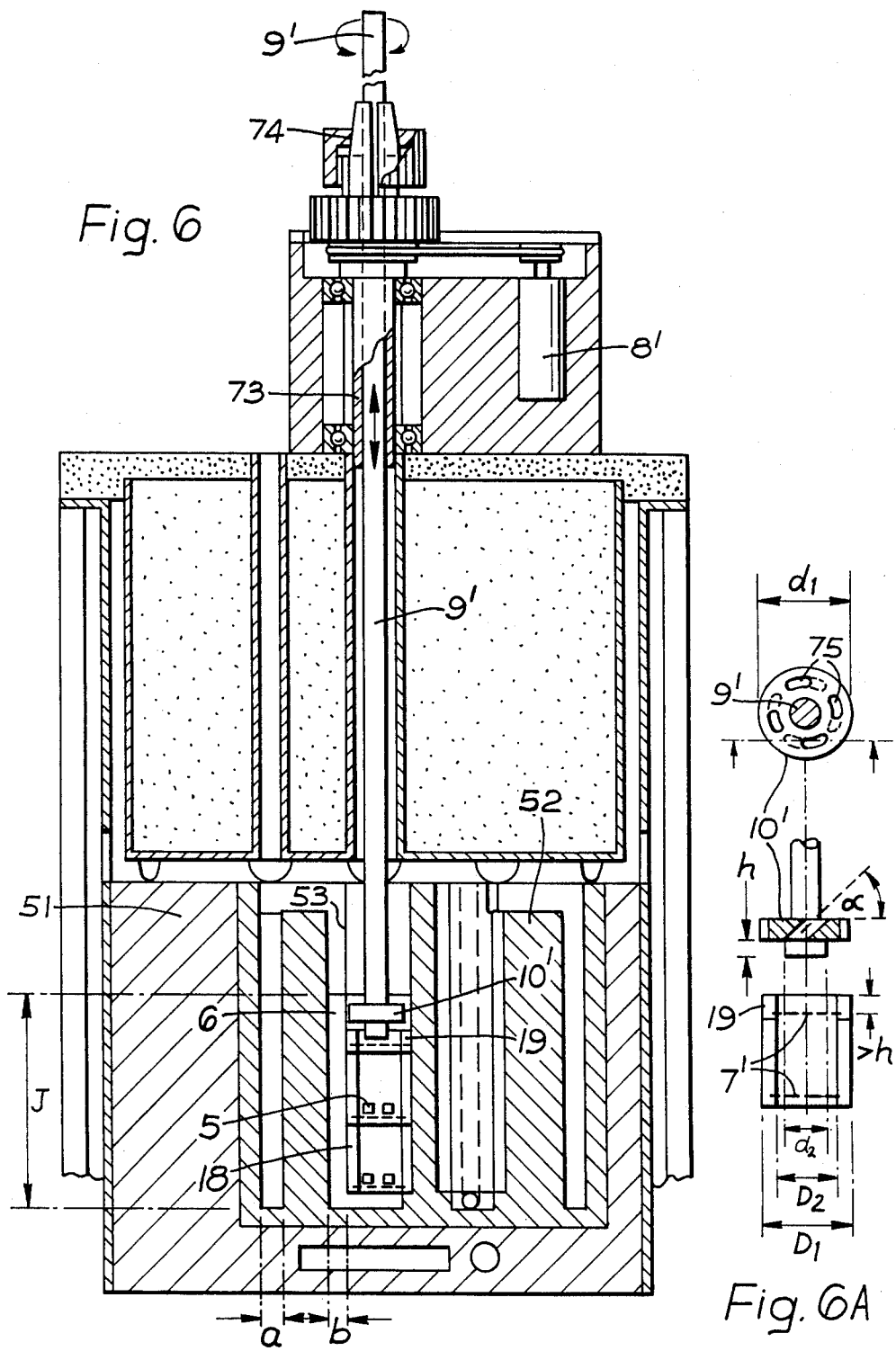

APPARATUS FOR TREATING SPECIMENS AT LOW TEMPERATURE

BACKGROUND OF THE INVENTION

This invention relates to apparatus for treating specimens, particularly biological specimens, at low temperatures for a subsequent microscopic, particularly electron microscopic, examination.

Biological specimens for microscopic, particularly electron microscopic, examinations are to an increasing extent frozen extremely rapidly (shock freezing) in order to stabilise rapidly the specimens. Afterwards the specimens may be subjected to dehydration to remove the water content, which is frequently over 90% of the weight of the specimens. This is achieved by incubating the specimens at low temperatures to exchange the water contained in the specimens for suitable organic solvents such as anhydrous acetone or methanol, or for suitable organic solutions such as $OsO_4$ and/or uranyl acetate in anhydrous acetone or methanol. The correct control of the initial phase of this exchange is very important, and the exchange is performed at temperatures which are generally not above $-80°$ C., at least during this initial phase. If temperatures above $-80°$ C. are employed, then changes in the molecular structure of the specimens may occur, and this would depreciate the value of subsequent examination.

For safety reasons the initial phase of the dehydration generally takes place in the temperature range between $-80°$ C. and $-120°$ C., which cannot be obtained with conventional refrigeration thermostats unless there is a large outlay for apparatus.

For electron microscopy, usually 1 to 10 tissue blocks with an individual volume of between 0.1 mm$^3$ and 10 mm$^3$ are subjected in one operation to such a dehydration; this may take between 3 days and 3 weeks, depending upon the size of the objects and the preselected temperature. During this period the temperature must not be allowed to exceed the limit value (which has to be determined for each specimen individually) because otherwise the molecular structure of the specimens may be changed so that it is no longer possible to use the subsequent examination to make valid scientific statements about the specimen structure in the normal living state ("in vivo").

An apparatus for treating specimens is described in German Offenlegungsschrift No. 3,042,578. According to this specification the container in which dehydration and/or embedding is carried out is suspended into the neck of a Dewar vessel so that the top of the container is substantially flush with the top rim of the Dewar neck, and in this way can be easily charged with the media for dehydration and/or embedding, and with the frozen specimens.

During the dehydration and embedding, the container and the Dewar neck are covered with an insulating cover, through which only the shaft of an agitator to stir the media, and electrical connections for temperature regulation, are passed. The temperature regulation is effected by means of a heating cartridge and a temperature sensor using an electrical regulation circuit.

The Dewar vessel contains liquid nitrogen, and for incubation temperatures up to about a minimum of about $-80°$ C. cooling by cold nitrogen boiling off continuously from the liquid nitrogen is sufficient. The cooling of the container is accelerated, for the start of the work only, by a "cold finger" which is adjustable in height, and which temporarily causes a more intense thermal flux out of the container by direct metallic contact with the liquid nitrogen.

This known apparatus is substantially superior in its efficiency and its simple construction to the cooling systems employed previously.

However, certain problems arise during the charging of the container with the dehydration media and with the frozen specimens. The media employed are all extremely hygroscopic and, particularly in the cooled state, attract water very rapidly from the moist room air; this renders a low temperature dehydration of the type required impossible. There is also a possibility that the shock frozen specimens become superficially warmed above $-80°$ C. during introduction, and that irreversible heat damage occurs in the well preserved marginal zones of the specimens. This zone is frequently only 10 microns deep, and damage to it depreciates the results of the low temperature deyhydration.

Further difficulties can arise when operating with media which are employed at temperatures at or below $-120°$ C., and the dehydration is followed by an embedding which has to be performed at about $-35°$ C. An example of such embedding is a LOWICRYL low temperature embedding (cf. "Resin development for electron microscopy and an analysis of embedding at low temperature" by Carlemalm et al, 1982, Volume 126, page 123 to 143). The initial cooling to $-120°$ C. cannot be performed without a metallic connection between the container and the liquid nitrogen, but this afterwards causes an intense boiling of the liquid nitrogen to commence in the higher temperature range at which the embedding is performed, and this boiling becomes uncontrollable due the the necessary counter heating of the container.

Moreover, the multiple exchange of the media which is necessary, for example, when a low temperature dehydration is followed by a low temperature embedding, together with the necessary transfer of the dehydrated specimens into a separate chamber for the low temperature embedding, presents such substantial problems that this promising and scientifically interesting method has hitherto only rarely been adopted.

SUMMARY OF THE INVENTION

An object of the present invention is to facilitate and simplify the treatment of specimens, particularly small biological specimens with an individual volume less than about 10 mm$^3$, for a subsequent microscopic, particularly electron microscopic, examination, and to provide a suitable apparatus for this purpose.

It is a further object of the invention to provide apparatus in which the introduction and manipulation of specimens, and the charging and exchange of treatment media can be performed more easily and more safely than has hitherto been possible, so that the treatment can be carried out over a temperature range of between $-150°$ C. and about $-30°$ C. without excessive cryogen consumption.

According to the present invention there is provided apparatus for treating biological specimens at low temperatures for subsequent microscopic examination comprising a vessel adapted to contain liquid coolant, a container having a specimen treatment chamber, said container being disposed within said vessel, and said specimen treatment chamber being adapted to receive a specimen to be treated and a specimen treatment medium, and precooling means for precooling the specimen treatment medium before it is introduced to the specimen treatment chamber.

Advantageously the precooling means is disposed in the vessel.

Preferably the precooling means comprises a reservoir communicating with the specimen treatment chamber, and delivery means for delivering the specimen treatment medium to the reservoir. The reservoir and delivery means can be advantageously arranged so that specimen treatment medium flowing through the reservoir and delivery means is cooled by the liquid coolant, and so that the specimen treatment medium can flow through the delivery means in countercurrent heat exchange with specimen treatment medium flowing from the reservoir to the specimen treatment chamber. This helps to ensure that the treatment medium reaches the specimen treatment chamber substantially at the required temperature.

Desirably an overflow is disposed at an upper end of the reservoir and the specimen treatment chamber communicates with the reservoir via said overflow, whereby specimen treatment medium can flow from the reservoir to the specimen treatment chamber when the level of said medium in the reservoir exceeds the level of the overflow.

Desirably the delivery means comprises a cannula extending into the reservoir. The vessel may be provided with a cover for insulating the interior of the vessel from an external environment; the cover may be provided with an aperture aligned with the reservoir, and the cannula may be arranged to extend through said aperture to the reservoir.

In a preferred construction an additional reservoir communicating with the specimen treatment chamber may be provided, and the cover may include an additional aperture aligned with the additional reservoir. Withdrawal means may be provided extending through the additional aperture and into the additional reservoir, whereby the specimen treatment medium can be withdrawn from the vessel through the withdrawal means.

The specimen treatment chamber may be disposed below the level of an upper rim of the vessel, thereby providing a space between the chamber and the level of the upper rim. A thermally insulating plug may be provided on the cover, to substantially fill the space between the chamber and the upper rim of the vessel. The uppermost part of the container may be located at least substantially 30 mm below the upper rim of the vessel.

Conveniently an agitator is provided extending into the specimen treatment chamber for agitating the specimen treatment medium; a temperature regulation device for regulating the temperature of the specimen treatment medium in the specimen treatment chamber may also be provided.

A heating element may be disposed in the liquid coolant, and may be actuatable to heat the liquid coolant to prevent precipitation of water on the specimen treatment chamber when the cover is removed, and to evaporate the liquid coolant to provide a stream of gaseous coolant flowing out of the vessel when the cover is removed thereby preventing the ingress of moist air from the external environment into the vessel. This helps to prevent frost precipitation and warming of the specimens when the cover is removed. The spacing of the specimen treatment chamber from the upper rim of the vessel also contributes towards this effect.

The apparatus may also include displacement means adapted to lift the cover, and delay means adapted to prevent operation of the displacement means until a preselected time after actuation of the heating element. The displacement means may comprise a reciprocating piston loaded by a spring; an electrically actuated detent may be provided for triggering the movement of the piston, and a valve may be provided for controlling the speed of movement of the piston.

The apparatus may further include a thermal insulation layer adapted to shield thermally the container from the liquid coolant. An element having high thermal conductivity may be arranged to extend into the coolant, a connecting member extending through the thermal insulation layer may be provided for connecting the specimen treatment chamber to the element.

Preferably the connecting member comprises a cylindrical tube having a cylindrical insert element slidably disposed therewithin and in good thermal contact therewith. Adjustment means may be provided for adjusting the vertical position of the cylindrical insert element in order to modify the thermal flux. The adjustment means may comprise, for example, an actuating rod and a spring arranged so that the insert element can be adjusted by moving the actuating rod counter to the pressure of the spring. The actuating rod may be detachable in order to facilitate removal of the cover from the vessel, and regulating means may be provided to regulate the position of the actuating rod.

Specimen treatment medium supply means may be provided having a large aperture to which the cannula can be secured. A filter is conveniently disposed within said supply means for withdrawing water from the specimen treatment medium before it enters the cannula.

In one embodiment the specimen treatment container may be provided with a plurality of the specimen treatment chambers and with a plurality of pairs of the reservoirs and the additional reservoirs, each of the specimen treatment chambers being in communication with one of the reservoirs, and with one of the additional reservoirs. A rotatable housing may be provided within which the specimen treatment chamber are arranged, so that upon its rotation through a prescribed angle one pair of the reservoir and additional reservoir can be brought into alignment with the aperture and the additional aperture in the cover.

A continuous bore may be provided for introducing liquid coolant into the vessel, and a thermally insulated plug may be provided at the end of the bore near the cover for closing the bore; the bore may extend through the cover and the specimen treatment container.

A vertically adjustable shaft may be provided which is secured to the agitator whereby the position of the agitator may be adjusted by vertical adjustment of the shaft.

Preferably, the agitator comprises a rotating member coaxial to the shaft having at least one bore extending along an axis from its upper side to its lower side, said axis being oriented obliquely to the axis of the shaft; the agitator may be dimensioned and shaped to minimise the amount of specimen treatment medium required.

A removable embedding insert may be provided, which is adapted to be disposed in the vessel above the specimen treatment container, for the purpose of low temperature embedding. The embedding insert may include depressions to receive embedding containers for the specimens, and may have a passage to the specimen treatment chamber to permit the transfer of the specimens from the specimen treatment chamber to the embedding containers.

An ultraviolet radiator may be removably secured to an underside of the cover, and a plate permeable to ultraviolet radiation may be provided between the radiator and the embedding insert. A temperature sensor may be disposed between the plate and the embedding insert to measure and regulate the temperature between the plate and the embedding insert.

A lamp may be disposed outside the vessel, and a pivotable mirror may be disposed on a bracket secured to the vessel, said mirror being pivotable between first and second positions. A switching element may be provided, which is actuatable to switch off the lamp. Preferably, when the mirror is in the first position it engages the switch thereby actuating the switching element and switching off the lamp, and when the mirror is in the second position it can deflect a light beam from the lamp onto the embedding insert.

In the apparatus according to the invention after the specimens have been introduced the entire treatment of the specimens can be performed without exposing the specimen treatment chamber to the external environment.

BRIEF DESCRIPTION OF THE DRAWINGS

Reference is now made to the accompanying drawings, in which:

FIGS. 1A and B show diagrammatical sectional elevations of two different embodiments of prior art apparatus with a liquid/gaseous nitrogen refrigeration system for dehydration and/or embedding of specimens at low temperatures;

FIG. 1C is a view on lines 1C—1C of FIG. 1B;

FIG. 1D is an axial section through a stack of specimen containers shown in FIG. 1B, on an enlarged scale;

FIG. 6 shows a diagrammatic sectional elevation of a fifth embodiment of part of an apparatus according to the invention;

FIG. 6A shows a plan view and an elevation of an agitator and of an associated specimen container shown in FIG. 6.

DESCRIPTION OF THE PREFERRED EMBODIMENTS

Figure 2:
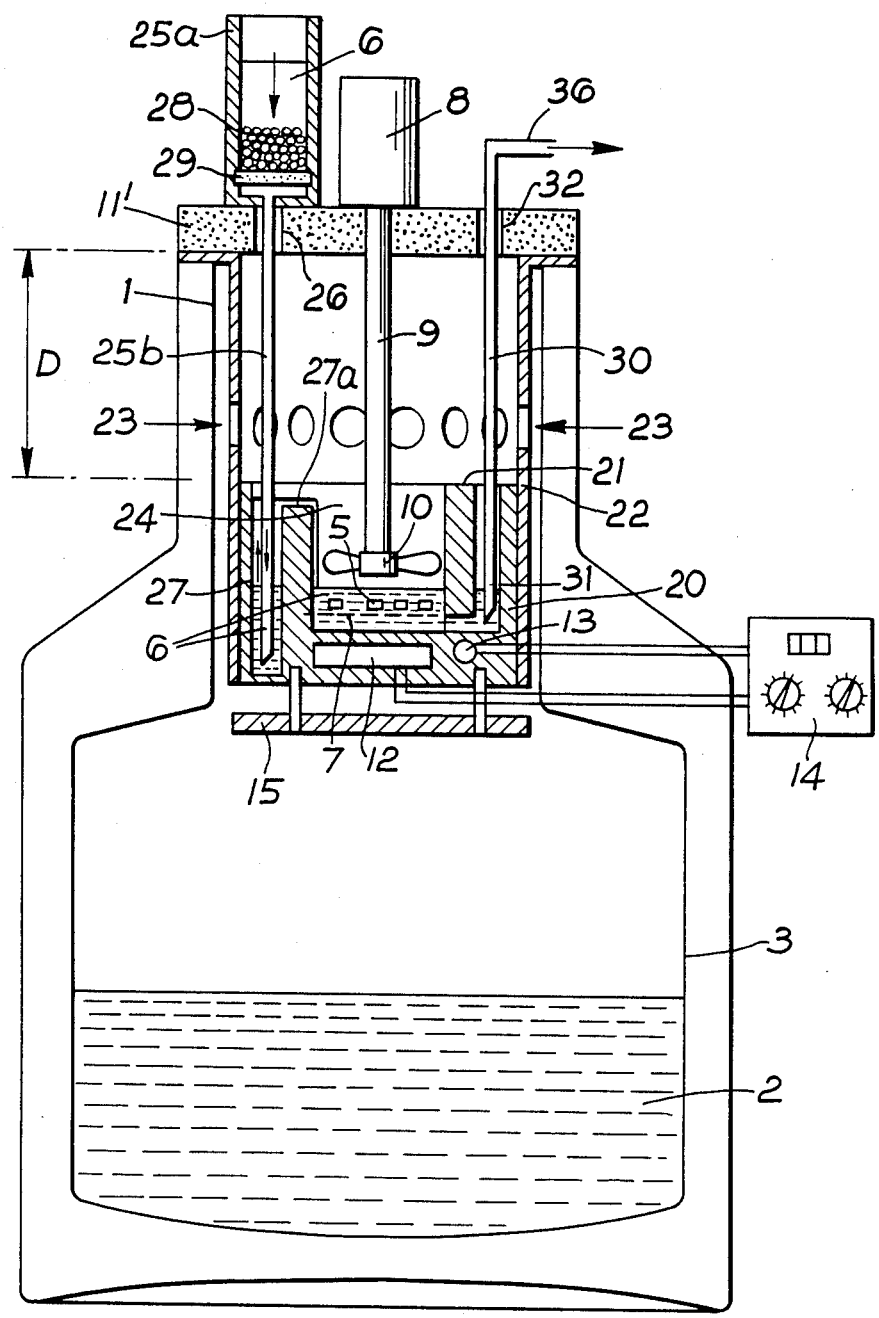
FIG. 2 is a diagrammatic sectional elevation of a first embodiment of an apparatus according to the invention.

FIG. 1A shows known apparatus for the dehydration and/or embedding of small biological specimens. A metallic container 4 with specimen treatment chamber 4a to receive specimens 5 and a specimen treatment medium 6 for the dehydration and/or embedding of the specimen 5, is located in a neck 1 of a Dewar vessel 3. The Dewar vessel 3 is filled with liquid coolant in the form of liquid nitrogen 2. The specimens 5 rest upon a mesh 7 in the container 4, so that they are washed continuously by the medium 6 from all sides. The mesh 7 serves to support the specimens 5 in the specimen treatment chamber 4a.

Circulation of the medium 6 is provided for by means of an agitator 10 driven by a motor 8 via a shaft 9.

The container 4 is closed during the dehydration and/or embedding by a cover 11 which has to be opened temporarily during the introduction of the specimens 5 and/or or the medium 6, and also when the medium 6 is changed.

The container 4 is disposed in gaseous nitrogen above the liquid nitrogen 2 and does not directly contact the liquid nitrogen. In the equilibrium state the container 4 attains a minimum temperature in the region of about $-80°$ C., which varies with the height H of the upper surface level of the liquid nitrogen 2 in the Dewar vessel 3. The temperature of the container 4 can be maintained constant (during steady state operation) at any value above this equilibrium value. Alternatively the temperature can be reproducibly varied as a temperature-time control system, by means of a heating cartridge 12 and of a temperature sensor 13 which are connected to temperature regulating apparatus 14.

A radiation shield plate 15 is provided between the container 4 and the liquid nitrogen 2. Where higher temperatures, for example in the range of above $-50°$ C. are used, the radiation shield plate 15 prevents a more intense boiling of the liquid nitrogen 2.

Lower temperatures can be obtained by establishing a metallically conductive connection between the container 4 and the liquid nitrogen 2; this is achieved by inserting a cylindrical rod 16 made of aluminum, for example, into the liquid nitrogen 2. The minimum obtainable temperature varies considerably depending on the distance A between the bottom of the container 4 and the upper surface level of the liquid nitrogen 2; the distance A is a function of the height H.

FIG. 1B shows an apparatus suitable for incubating simultaneously a plurality of specimens 5. In FIG. 1B a container 4' is provided with a plurality of specimen treatment chambers 17. Each specimen treatment chamber 17 is substantially cylindrical and can receive a plurality of stacked small specimen containers 18. The bottom of each of small specimen container 18 is provided with a mesh 7', upon which the specimens 5 are placed and supported. Each stack of small containers 18 is covered by a cover 19 having a mesh 7', so that the specimens 5 in the uppermost of the specimen containers 18 cannot be washed out of the container 4', even when the agitator 10 is rapidly rotated.

FIGS. 2 to 7 show embodiments of the apparatus according to the invention. A number of the parts in FIGS. 2 to 7 are similar to those shown in FIGS. 1A and 1B, and like reference numerals are used to designate like parts.

The apparatus shown in FIG. 2 is provided with a specimen treatment container 20 which, like the containers 4 and 4' shown in FIGS. 1A and 1B, is disposed in the neck 1 of the Dewar vessel 3; the Dewar vessel 3 is filled with liquid nitrogen 2. The container 20 is provided with a cylindrical specimen treatment chamber 24. An uppermost part 21 of the container 20 is arranged at least 30 mm below the top rim of the neck 1 of the Dewar vessel 3 (indicated by D in FIG. 2), and is maintained in the neck 1 by a thin walled tube 22, which may be made, for example, of stainless steel. The tube 22 is provided with a ring of apertures 23.

The apparatus is provided with precooling means for precooling the specimen treatment medium 6 before it is introduced into the specimen treatment chamber 24. The precooling means comprises a reservoir in the form of a bore 27 and delivery means in the means of a cannula 25b, one end of which extends into the bore 27 adjacent the bottom of the bore 27. The end of the cannula 25b opposite from the end extending into the bore 27 communicates with specimen treatment medium supply means in the form of a charging cylinder 25a.

The top rim of the bore 27 forms an overflow 27a to the specimen treatment chamber 24. An additional reservoir in the form of a further bore 31, which is constructed in the container 20 on the opposite side to the bore 27, communicates at its lower part with the specimen treatment chamber 24.

The Dewar neck 1 is closed by a cover 11', which is provided with apertures 26 and 32; the aperture 26 is aligned with the bore 27, and the aperture 32 is aligned with the bore 31. The cannula 25b extends through the aperture 26, and withdrawal means in the form of a second cannula 30 extends into the bore 31 through the aperture 32.

Before the apparatus shown in FIG. 2 is operated, the bores 27, 31 and the specimen treatment chamber 24 are empty of specimen treatment medium 6, and the Dewar vessel 3 is empty of liquid nitrogen 2. Operation is begun by removing the cover 11', then pouring liquid nitrogen 2 through the Dewar neck 1 into the tube 22 which cools and fills the container 20 and the tube 22, and then flows through the apertures 23 into the Dewar vessel 3. The container 20 and the tube 22 then initially remain filled with liquid nitrogen 2 up to the level of the apertures 23, into which the frozen specimens 5 for treatment, for example by dehydration, can be introduced safely using a small container (not shown). The specimens 5 are placed on the mesh 7 within the specimen treatment chamber 24 below the surface level of liquid nitrogen 2 in the tube 22. The cover 11' is then closed, and the liquid nitrogen 2 is evaporated out of the container 20 and of the tube 22 using the temperature regulating apparatus 14, the temperature sensor 13, and the heating cartridge 12; the container 20 can be warmed up to the temperature preselected for the treatment. After this temperature has reached the specimen treatment medium 6, which is at room temperature, is poured into the charging cylinder 25a. The specimen treatment medium 6 flows from the charging cylinder 25a through the cannula 25b to the bore 27.

The bore 27 and the cannula 25b are arranged so that specimen treatment medium 6 flowing through the bore 27 and the cannula 25b is cooled by the liquid nitrogen 2, and so that the specimen treatment medium 6 flows through the cannula 25b in countercurrent heat exchange with the specimen treatment medium 6 flowing from the bore 27 to the specimen treatment chamber 24 via the overflow 27a. The inside diameter of the cannula 25b, and that of the bore 27, are dimensioned so that the specimen treatment medium 6 flows in so slowly that it becomes cooled to the preselected temperature of the container 20 during the countercurrent movement within the bore 27 and overflows into the specimen treatment chamber 24 only after this temperature is attained. The thermal capacity of the entire quantity of the specimen treatment medium 6 is less than 5% of the thermal capacity of the precooled container 20, so the container 20 becomes warmed only slightly during the cooling of the specimen treatment medium 6.

A molecular sieve 28 is disposed in the cylinder 25a upon an interposed filter 29, so that the specimen treatment medium 6 can be provided in a totally anhydrous state if necessary, for example when a subsequent elemental analysis is to be performed.

In order to change the medium 6, the medium 6 can be sucked out of the specimen treatment chamber 24 through the second cannula 30 via the bore 31 in the container 20, without the need to open cover 11'. Thus, the entire treatment can be performed without removing the cover 11'. For example, in the case of a normal cryosubstitution in acetone/OsO$_4$ or methanol/OsO$_4$/uranyl acetate, followed by Lowicryl monomer embedding, all the steps of the treatment can be performed without opening the cover 11', and without the danger of a water precipitation and/or an uncontrollable heating of the specimens 5 which exists in the case of the conventional type of apparatus shown in FIGS. 1A and 1B.

Gaseous nitrogen which continuously evaporates from the liquid nitrogen 2 passes through the apertures 23 into the interior of the tube 22 and thus maintains the space above the container 20 at a low temperature.

Figure 3:
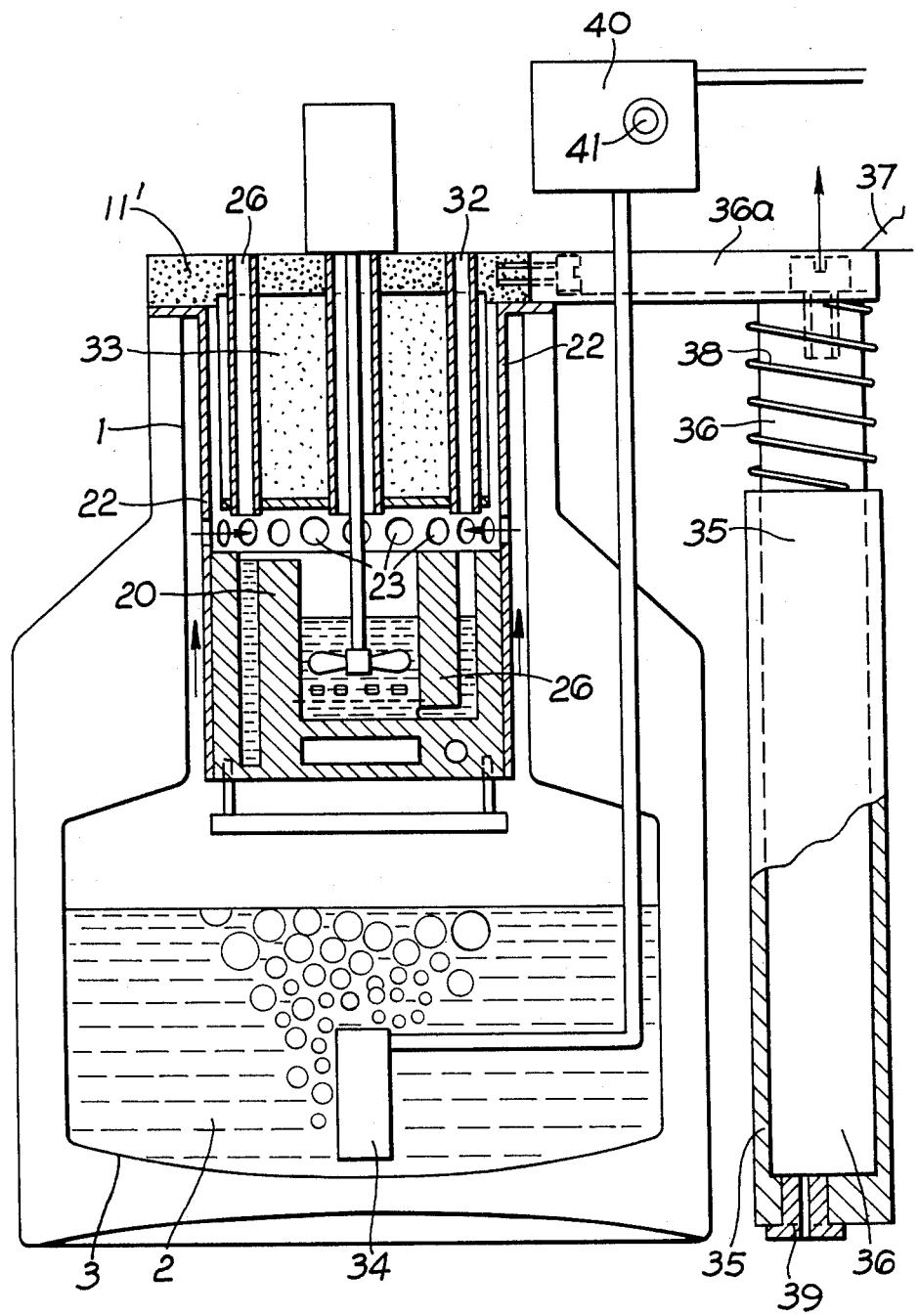
FIG. 3 is a diagrammatic sectional elevation of a second embodiment of an apparatus according to the invention.

The embodiment shown in FIG. 3 permits a routine and repeated opening of the apparatus for the purpose of the withdrawal of dehydrated specimens 5, and for charging with fresh frozen specimens 5. A substitution of methanol/OsO$_4$ can be performed within 6 hours, and this embodiment is particularly appropriate to the requirements of daily routine.

In this embodiment the dead space present above the container 20 is filled with a plug 33 of thermally insulating material in order to assist in preventing moist room air entering the Dewar neck 1 when the cover 11' is opened and causing frost precipitation on the container 20 and on the tube 22. The plug 33 is connected to the cover 11' in any desired manner and is operable conjointly with the latter.

A heating cartridge 34 is arranged in the liquid nitrogen 2 and acts as an evaporator.

When the heating cartridge 34 is switched on, the liquid nitrogen 2 is heated by the heating cartridge 12 and evaporates in large quantities. The evaporated gaseous nitrogen flows through the apertures 23 of the tube 22 and fills the space vacated by the plug 33 when the cover 11' is raised; this prevents the ingress of moist room air. This additionally ensures an inert, dry and cold gas atmosphere when charging the container with frozen specimens 5. The best results can be achieved when the heating cartridge 34 is switched on before removal of the cover 11', so that the tube 22 is filled with gaseous nitrogen before the cover 11' is removed.

The cover 11' may be removed and replaced manually. However, it is preferred to operate the removal of the cover mechanically, whereby the cover 11' is raised automatically at a minimum speed. One way of achieving this would be to use a servomotor, for example. Alternatively the mechanical system illustrated in FIG. 3 can be used. This comprises displacement means in the form of a hollow column 35, which is attached in a manner not shown in detail adjacent the Dewar vessel 3. The displacement means also includes a shank 36 slidably disposed within the hollow column 35 and the outer surface of the shank 35 is in fluid tight engagement with the inner surface of the hollow column 35; this provides a "piston" arrangement which is connected to the cover 11' by a yoke 36a. The yoke 36a is bolted to the shank 36 and is stressed upwardly by a pretensioned compression spring 38. The shank 36 is maintained in a position which corresponds to the closed state of the cover 11' by a detent 37. A valve 39 is disposed at the base of the hollow column 35 and permits an inflow of air into the interior of the hollow column 35 through a throttled orifice.

When the detent 37 is released the slidable shank 36 together with the yoke 36a and the cover 11' is raised by the spring 38. The valve 39 permits a slow admission of air into the interior of the hollow column 35 during the upward stroke of the shank 36, whereby the cover 11' is slowly raised. During the subsequent descent of the cover 11', the valve 39 permits the air to exit again rapidly from the hollow column 35.

An electronic system 40 may be provided for controlling the heating cartridge 34 and the automatic cover lifting mechanism. The electronic system 40 includes an opening button 41. When the button 41 is pressed the heating cartridge 34 is switched on through the electronic system 40, and after a time delay the detent 37 is tripped electrically. In this way the lifting of the cover 11' occurs automatically with the required delay after the switching on of the heating cartridge 34, and without further intervention by the operator. The electronic system 40 includes delay means which permits the delay to be pre-selected.

The apertures 26 and 32 in the cover 11' also extend through the plug 33, so that the charging and the exchange of the medium 6 can be performed in the same manner as has already been described above.

Figures 4, 4A:
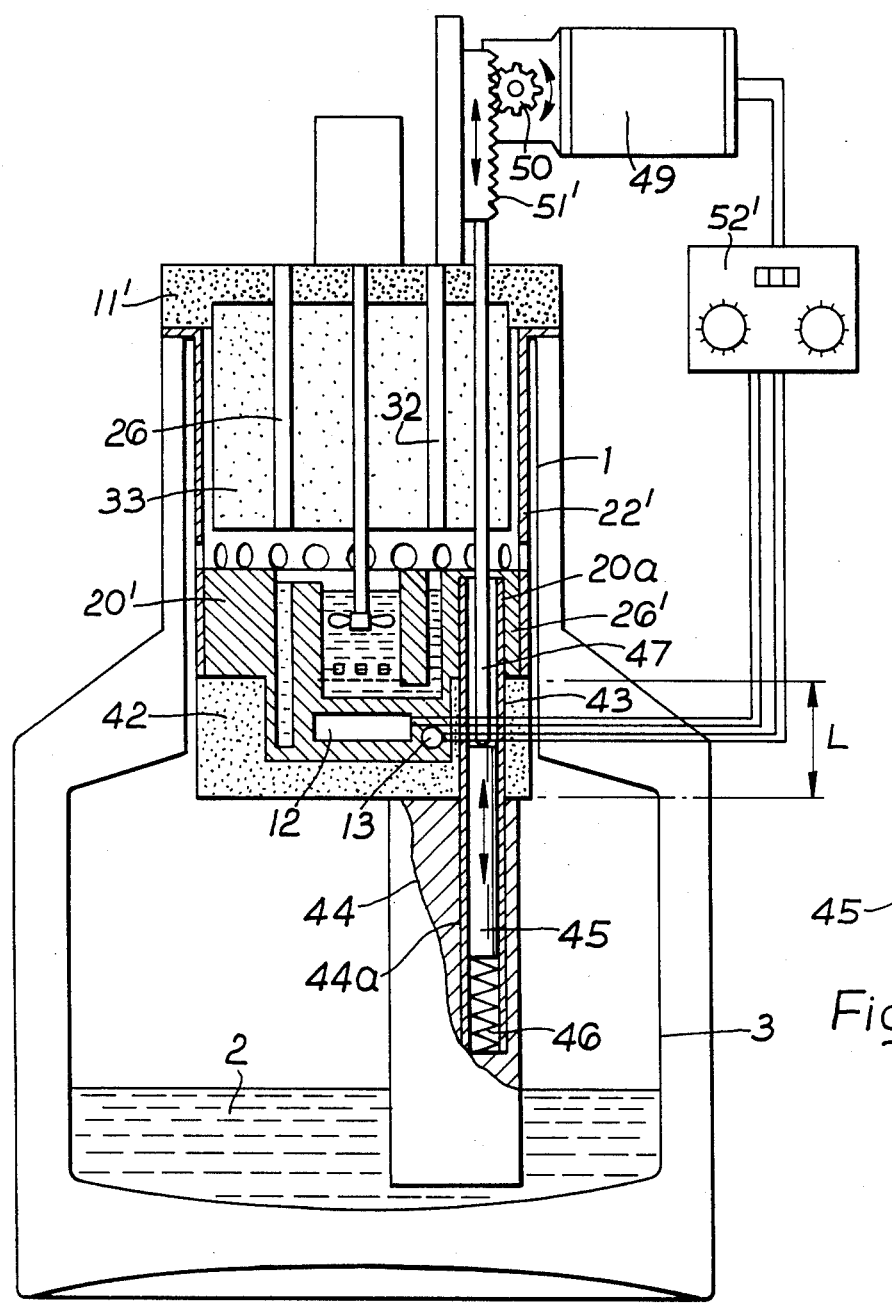
FIG. 4 is a diagrammatic sectional elevation of a third embodiment of an apparatus according to the invention.
FIG. 4A is a partial section of an insert element shown in FIG. 4.

The embodiment illustrated in FIG. 4 is particularly suitable for treating specimens at the very low or high incubation temperatures which are often necessary in the course of a single operation in the case of a cryo substitution at −120° C. with subsequent low temperature incubation at −30° C. Metallic contact with the liquid nitrogen 2 is necessary in order to achieve the desired low temperatures around −120° C. Furthermore, it is necessary to provide very good thermal insulation between the liquid nitrogen 2 and the specimen treatment container designated 20' in order to achieve the higher temperatures of about −30° C.

In order to meet these requirements the container 20' is, at least in its lower half, thermally insulated relative to the liquid nitrogen 2 by a thermal insulation layer 42, made of polyurethane hard foam for example. A connecting member including thin walled metallic sleeve 43, which is retained in a bore 20a of the container 20', projects through the insulation layer 42 into a corresponding bore 44a of a massive metal element 44 and establishes a metallic contact between the container 20' and the massive metal element 44.

The massive metal element 44 is made of a material with good thermal conductivity (such as aluminum for example) and the entire material of the element 44 is at substantially the boiling point of the liquid nitrogen 2, irrespective of the charge level of liquid nitrogen 2 in the Dewar vessel 3. The temperature of the container 20' varies according to the length L, the cross-sectional area and the thermal conductivity of the sleeve 43.

The temperature of the container 20' can be adjusted to a preselected value, for example, by tubular insert elements (not shown) which may be slid into the sleeve 43. The cooling system can in this way be adapted to different operating conditions without major outlay.

FIG. 4 shows an alternative way of adjusting the temperature of the container 20' to a preselected value during treatment without having to open the apparatus. For this purpose the connecting member further includes a cylindrical insert element 45 slidably disposed in the sleeve 43 in a close fit with the metallic inner wall of the sleeve 43. The element 45 is movable up and down using adjustment means comprising a spring 46 and a rod or tube 47. The element 45 is movable up and down counter to the thrust of the compressed spring 46 which is disposed between the base of the element 45 and the base of the bore 44a, by means of the rod or tube 47. FIG. 4A shows a cylindrical hole 48 in such an insert element 45, by means of which a very precise variation of the loss of heat from the container 20' to the metal element 44 is made possible.

The upward and downward movement of the insert element 45 may be achieved manually. However, FIG. 4 illustrates a mechanical regulating means for achieving this movement. The regulating means includes a rack transmission comprising a toothed wheel 50, and a rack 51', which engages the rod or tube 47. The toothed wheel 50 is driven by a motor 49. The teeth of the toothed wheel 50 engage the teeth of the rack 51' so that rotation of the toothed wheel 50 in one direction causes upward movement of the rack 51' and rotation of the toothed wheel 50 in the opposite direction causes downward movement of the rack 51'.

A regulating unit 52', connected to the temperature sensor 13 and the heating element 12, is also connected to the motor 49 so that the liquid nitrogen 2 consumption can be minimised by regulation of the loss of heat from the container 20'. The upward and downward movement of the rod or tube 47 is controlled as a function of the temperature of the container 20' measured by the temperature sensor 13.

Figure 5A:
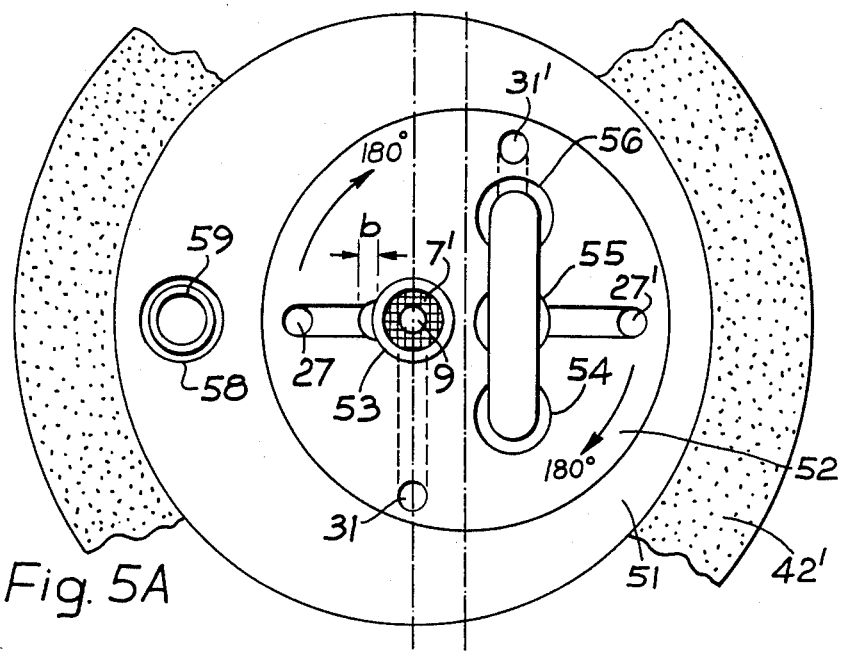
FIGS. 5A and 5B show respectively a diagrammatic plan view and a diagrammatic sectional elevation of part of a fourth embodiment of an apparatus according to the invention, on a larger scale than the apparatusses shown in FIGS. 2 to 4.

FIGS. 5A and B show an embodiment in which a plurality of specimens may be simultaneously treated in the same apparatus. The apparatus can be readily adapted to treat different numbers of specimens.

As described above, small specimens with a volume of less than 10 mm$^3$ are usually processed in small numbers when treated by dehydration or embedding at low temperature. In this case only a few blocks are usually dehydrated and embedded in one operation. In view of the expensive $OsO_4$ which is often used in high concentration as an additive to the dehydration medium, it is desirable to perform the treatment with the smallest possible quantity of liquid. However, the number of specimens required for treatment at a particular time tends to vary considerably.

Figure 5B:
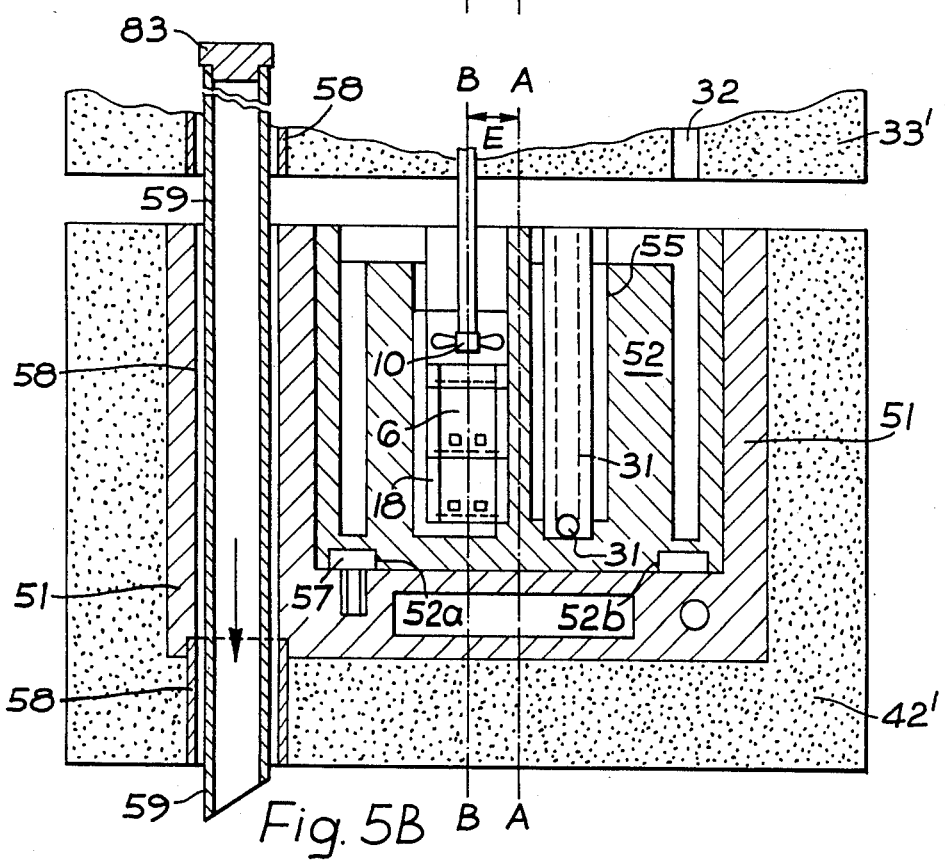

The embodiment illustrated in FIGS. 5A and 5B is capable of meeting these varied requirements. A specimen treatment container 52 is of cylindrical construction and is arranged rotatably about a vertical axis A—A in a metallic housing part 51. The axis A—A of the container 52 is located parallel to a median axis B—B of the housing part 51 and eccentrically thereto by an amount E. The cover covering the container 52 and the Dewar neck is not shown in FIGS. 5A and 5B, but is provided with the apertures described in connection with FIG. 2 for introducing and withdrawing the medium 6, and for the agitator shaft 9.

The container 52 is provided with a housing tube 53 which serves as a specimen treatment chamber. The housing tube 53 communicates with the charging bore 27 via an overflow. The axis of the housing tube 53 is arranged at the interval E from the axis of rotation A—A of the container 52.

A tube system consisting of three mutually communicating tubes 54, 55 and 56 is arranged on the opposite side of the axis A—A to the tube 53. The central tube 55 of the tubes 54, 55 and 56 is arranged at the distance E from the axis A—A. The tubes 54, 55 and 56 communicate with a charging bore 27' and withdrawal bore 31'. The tubes 54, 55 and 56 are chargeable with medium 6 via the charging bore 27'.

The medium 6 can be withdrawn from the housing tube 53 via the bore 31 and from the tubes 54, 55 and 56 via the bore 31' without releasing the cover, in the same way as has already been described in connection with the previous embodiments.

Two mutually opposite bores 52a and 52b are provided in the lower end face of the container 52. One at a time of the bores 52a and 52b can co-operate with detent means 57 which extends into the bottom of the housing part 51, in order to fix the rotary position of the container 52; the detent means 57 may, for example, be a bolt.

After retraction of the detent means 57, the container 52 can be rotated about the axis A—A through 180°. This moves the housing tube 53 out of the position shown in FIG. 5A, and moves the tube 55 of the tubes 54, 55 and 56 into the centre (i.e. on the axis B—B) of the housing part 51.

It is now possible for the agitator 10 with the agitator shaft 9, which dips into the single housing tube 53 when the container 22 is in the position shown in FIGS. 5A and B, to dip into the central tube 55 of the tubes 55, 56 and 57. Likewise the charging bore 27 and the withdrawal bore 31 are moved out of alignment with the corresponding apertures in the cover, and the bores 27' and 31' are moved into alignment with the corresponding apertures in the cover. The bores 27 and 31 are arranged in mirror-image symmetry with the bores 27' and 31', so that after the 180° rotation about the axis A—A, the charging and drainage of the tubes 54, 55 and 56 can be performed through the same apertures in the cover as the charging and drainage of the housing tube 53 before the 180° rotation of the container 52. The correct respective position of the container 52 is ensured by the engagement of the detent means 57 into the corresponding bore 52a or 52b of the container 52.

It is possible with the apparatus shown in FIGS. 5A and 5B to process a smaller number of specimens by using the housing tube 53 alone, whereas the use of the tubes 54, 55 and 56 permits the processing of a larger number of specimens.

In FIGS. 5A and 5B a continous vertical bore 58 extends through the cover 11' through the plug 33', through the metallic housing part 51, and through the thermal insulating layer 42' surrounding the housing part 51. The bore 58 is closed by a thermally insulated plug 83 on the surface of the cover 11', and is preferably reinforced by metal tubes. When the thermally insulating plug in the surface of the cover 11' is open, a tube 59 for introducing fresh liquid nitrogen 2 into the Dewar vessel 3 may be slid through the bore 58, so that the Dewar vessel 3 can be topped up with particularly useful in when needed, without interrupting the treatment process taking place. This topping up is particularly useful in the cases where substitution is made with apolar hydrophobic media (for example ether or chloroform) for the purpose of a subsequent elemental analysis of water soluble ions of alkali or alkaline earth metals. Due to the low affinity between these media and the $H_2O$ molecule, such substitution processes frequently require several weeks, and cannot be completed without the intervening topping up with liquid nitrogen 2 which is made possible by the above described development.

As explained above, where only a few specimens 5 are substituted, it is desirable that the quantity of the medium 6 containing expensive materials such as $OsO_4$ should be kept as small as possible in order to keep costs to a minimum. The embodiment shown in FIG. 6 is particularly suitable for meeting this requirement. The embodiment shown in FIG. 6 is a modification of the embodiment shown in FIG. 5 and like parts have been designated with like reference numerals. In the embodiment shown in FIG. 6 it is possible to keep the height of the liquid column J in the housing tube 53 of the container 52 as low as possible. The height J can be adapted precisely to the number and/or the height of the stacked containers 18 and the cover 19.

In order to achieve this it is important that the vertical position of the agitator 10' can be adjusted. It is also important that the vertical position of the agitator 10' is adjustable from outside the apparatus without opening the cover 11', and that the geometrical shape of the agitator 10' restricts the dead space not directly required for the substitution. For this purpose the agitator shaft 9' is slidable up and down vertically in a sleeve 73 and can be fixed in any desired vertical position by means of clamping apparatus; the clamping apparatus may include a collet 74, for example. The agitator shaft 9' is driven, through a transmission engaging the sleeve 73, by a motor 8'.

FIG. 6A shows the construction of the agitator 10' in greater detail. In order to reduce the dead space and to increase the stability of the agitator 10', it is not constructed in the customary manner as a propellor, but as a rotary part with a closed circumference, the diameters $d_1$, $d_2$ of which are adapted to corresponding diameters $D_1$, $D_2$ of the small specimen containers 18 and/or of the covers 19 for the specimen containers 18. Likewise, the height h of a lug projecting downwards from the agitator 10' is dimensioned so that, when the collet 74 is released, the agitator 10' can safely be pushed down from the outside via the shaft 9' into the mechanical contact with the cover 19. After this contact, the shaft 9' can be raised visibly (by eye measurement for example) by the small amount which just ensures the free running of the agitator 10' within the medium 6. The geometrical shape of the container 18 and of the agitator 10' are experimentally suitably adapted and optimised, so that where only a few specimens 5 are being substituted in a single container 18, a quantity of liquid of approximately 2 ml is sufficient for a substitution in this embodiment.

The convection of the medium 6 is produced by inclined bores 75 in the disc forming the agitator 10', the axis of each bore 75 being oriented at an angle to the axis of the agitator shaft 9'.

In the embodiment of FIGS. 5 and 6, a groove of depth b is milled on the side of the housing tube 53 extending along the length of the tube 53, in order to permit a circulation of the medium 6.

Figure 7:
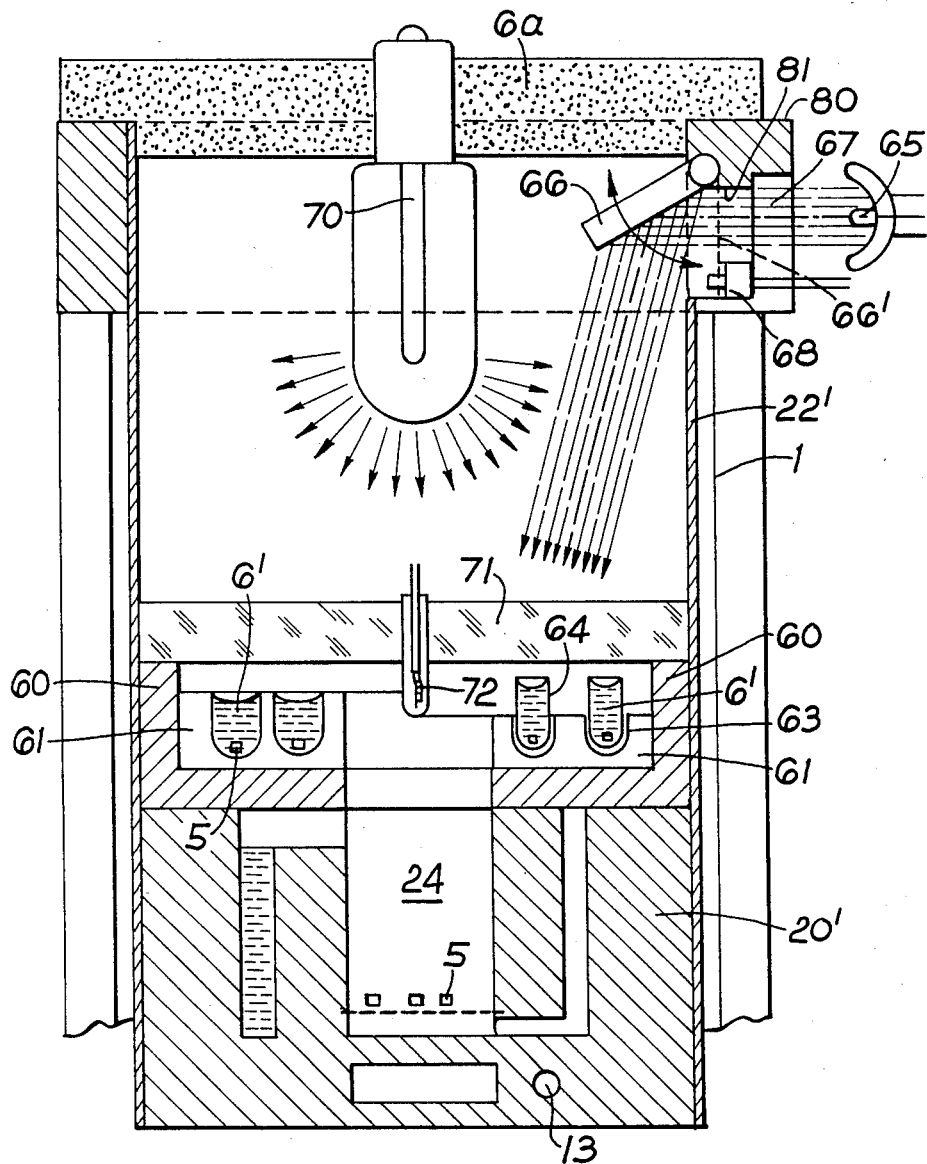
FIG. 7 shows a diagrammatic sectional elevation of part of an apparatus according to the invention in which means for polymerisation embedding is arranged above a specimen container.

A low temperature dehydration is frequently required to be directly followed by a low temperature embedding (in LOWICRYL for example). The apparatus according to the invention can immediately be equipped and adapted for this purpose as is shown in FIG. 7.

A cup-shaped insert 60 can be inserted into the space bounded by the container 20' and by the tube 22. The insert 60 may be metallic and forms a good thermal contact with the surface of the container 20' so that it assumes substantially the preselected temperature of the container 20'. A further insert 61, which is received in the insert 60, is provided with holes 63 in its surface, which serve either directly to accommodate the specimens 5 or to accommodate embedding containers 64. The embedding containers 64 may be gelatine or polyethylene capsules, for example, and the specimens 5 may be introduced into these containers 64.

The monomer initial product (monomer preparation) 6' for the low temperature embedding is charged either directly into the holes 63, or into the embedding containers 64, above the specimens 5. As is clear from FIG. 7, both inserts 60 and 61 are provided with a central passage which permits access to the specimen chamber 24 of the container 20' to facilitate the withdrawal of the incubated specimens 5 from the specimen chamber 24, and their transfer into the depressions 63 and/or into the embedding containers 64 within the Dewar neck.

In practice these manipulations present certain difficulties because the relatively narrow aperture of the Dewar neck 1 does not permit adequate illumination. To remedy this problem the embodiment shown in FIG. 7 is provided with illumination by a light source 65, which is arranged outside the Dewar neck 1. The light source 65 may be secured to the neck 1 by conventional means.

The tube 22' is connected at its upper end to an annular attachment 80, in which an aperture 81 is provided. A mirror 66 is disposed in the aperture 81 so that it can pivot about a substantially horizontal axis. A heat blocking filter 67, which is adapted to substantially eliminate the infrared component of the light source 65, is arranged between the light source 65 and the mirror 66 in the aperture 81. The mirror 66 permits a beamed projection of the light of the light source 65 into the operating space above the inserts 60 and 61. The mirror 66 is arranged to one side of the neck 1 and in no way obstructs the preparatory operations, for example the introduction of the specimens 5 into the chamber 24, the charging of the specimens 5 into the small containers 18, or the transfer of the Specimens 5 into the holes 63 or the embedding containers 64.

When the cover 11' and the thermally insulated plug 33' (not shown in FIG. 7) is closed, the mirror 66 is automatically pivoted back into a rest position 66' indicated by dashed lines. A microcontact 68 is provided in order to switch off the illumination automatically. When the mirror 66 is in the rest position 66', the microcontact 68 is biased towards the rest position which causes the light source 65 to be switched off.

After the introduction of the specimens 5 and of the monomer preparation 6', or of the embedding containers 64, an attachment 69 with an ultraviolet radiator 70 may be attached to the Dewar neck 1, or on to the top end of the tube 22', instead of the cover 11', for a subsequent ultraviolet polymerisation. The polymerisation chamber is bounded by the attachment 69, the tube 22' and the inserts 60 and 61. When necessary the upward end of the polymerisation chamber may be closed by a quartz glass plate 71 which is provided with a temperature sensor 72. The temperature sensor 72, in combination with a temperature regulating device (not shown), enables the polymerisation temperature in the polymerisation chamber present beneath the quartz glass plate 71 to be maintained constant. The temperature sensor 72 replaces the temperature sensor 13 which measures the temperatures of the container 20, so that the regulating device provided for regulation must be changed accordingly.

The insert 60 consists of a metal with good thermal conductivity, whereas the insert 61 consists of an anti-adhesive plastic material, for example silicone rubber or Teflon, and can easily be adapted to the particular requirements of each treatment.

The apparatus described with reference to FIGS. 2 to 7 may be modified or varied.

For example the particular form of the heating element the temperature sensors and the temperature regulators is not important, and the position at which they are installed in the apparatus can be varied according to requirements.

Futhermore, the principle illustrated in FIG. 5 may be realised in a number of different ways. Thus, with different differently chosen symmetries of the charging and withdrawal bores 27 and 31, a tube system suitable for accommodating the specimens may be brought into the central axis B—B, which corresponds to the axis of the agitator shaft 9, after a rotation by only 120° or 90° instead of a rotation by 180°.

The volume of all those spaces of the apparatus which are charged with medium 6, but do not serve directly for the incubation process, should be kept as small as possible. This applies for example to the charging bore 27 or 27', the diameter of which should be sufficiently small so that the countercurrent heat exchange effect described in connection with FIG. 2 develops, and to the groove of depth B (shown in FIGS. 5A and 6) which is only large enough for an adequate circulation of the medium 6.

I claim:

1. Apparatus for treating biological specimens at low temperatures for subsequent microscopic examination comprising:

a vessel adapted to contain liquid coolant, means defining a specimen treatment chamber for holding a specimen treatment medium and for receiving a specimen to be treated, said chamber-defining means being positionable within said vessel, and precooling means for precooling the specimen treatment medium before it is introduced to the specimen treatment chamber, said precooling means including means defining a reservoir communicating with the specimen treatment chamber and through which the specimen treatment medium is directed en route to the specimen treatment chamber and delivery means for introducing the specimen treatment medium into the reservoir, said reservoir being positionable within said vessel so that the walls of said reservoir are cooled by the liquid coolant contained within said vessel and so that the specimen treatment medium directed through said reservoir is cooled by the walls of said reservoir, said delivery means including a tube through which the specimen treatment medium is directed when introduced into said reservoir, said tube having a section arranged within said reservoir so that specimen treatment medium flowing through said tube section is cooled by specimen treatment medium flowing through said reservoir between the walls of said reservoir and the walls of said tube section.

2. Apparatus according to claim 1 wherein the tube section of the delivery means is arranged within said reservoir so that specimen treatment medium flowing through the tube section of the delivery means flows in countercurrent heat exchange relationship with specimen treatment medium flowing through the reservoir between the walls of said reservoir and the walls of said tube section.

3. Apparatus according to claim 2 wherein an overflow is disposed at an upper end of the reservoir and the specimen treatment chamber communicates with the reservoir via said overflow, whereby specimen treatment medium can flow from the reservoir to the specimen treatment chamber when the level of said medium in the reservoir exceeds the level of the overflow.

4. Apparatus according to claim 3 wherein the tube section of said delivery means is in the form of a cannula extending into the reservoir, the vessel is provided with a cover for insulating the interior of the vessel from an external environment, the cover is provided with an aperture aligned with the reservoir, and the cannula extends through said aperture to the reservoir.

5. Apparatus according to claim 4 wherein the specimen treatment chamber is disposed below the level of an upper rim of the vessel, thereby providing a space between the chamber and the level of the upper rim.

6. Apparatus according to claim 1 further comprising an agitator extending into the specimen treatment chamber for agitating the specimen treatment medium, and a temperature regulation device for regulating the temperature of the specimen treatment medium in the specimen treatment chamber.

7. Apparatus according to claim 4, wherein specimen treatment medium supply means is provided having a large aperture to which the cannula is secured, and a filter is disposed within said supply means for withdrawing water from the specimen treatment medium before it enters the cannula.

8. Apparatus for treating biological specimens at low temperatures for subsequent microscopic examination comprising:

a vessel adapted to contain liquid coolant and including a cover for insulating the interior of the vessel from an external environment, said cover provided with two apertures;

a container having a specimen treatment chamber, said container being disposed within said vessel, and said specimen treatment chamber being adapted to receive a specimen to be treated and a specimen treatment medium;

precooling means for precooling the specimen treatment means before the medium is introduced to the specimen treatment chamber, the precooling means including one reservoir communicating with the specimen treatment chamber and delivery means for delivering the specimen treatment medium to the one reservoir, said one reservoir and delivery means being arranged relative to one another so that specimen treatment medium flowing through the delivery means is in countercurrent heat exchange relationship with specimen treatment medium flowing from the one reservoir to the specimen treatment chamber, said one reservoir including an overflow disposed at the upper end thereof and the specimen treatment chamber communicates with the one reservoir via said overflow so that specimen treatment medium can flow from the one reservoir to the specimen treatment chamber when the level of said medium in the one reservoir exceeds the level of the overflow, said delivery means including a cannula extending into the one reservoir, one aperture of the cover being aligned with the one reservoir and the cannula extends through said one aperture to the one reservoir;

means defining an additional reservoir communicating with the specimen treatment chamber, the other aperture of the cover being aligned with the additional reservoir; and withdrawal means extending through said other aperture of the cover and into the additional reservoir so that specimen treatment medium can be withdrawn from the specimen treatment chamber through the withdrawal means.

* * * * *